United States Patent
Lin et al.

(10) Patent No.: US 11,020,024 B2
(45) Date of Patent: Jun. 1, 2021

(54) SYSTEM AND METHOD FOR EVALUATING RANGE OF MOTION OF A SUBJECT

(71) Applicant: KONINKLIJKE PHILIPS N.V., Eindhoven (NL)

(72) Inventors: Hong Lin, Suzhou (CN); Yugang Jia, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 14/759,810

(22) PCT Filed: Jan. 7, 2014

(86) PCT No.: PCT/IB2014/058087
§ 371 (c)(1),
(2) Date: Jul. 8, 2015

(87) PCT Pub. No.: WO2014/108824
PCT Pub. Date: Jul. 17, 2014

(65) Prior Publication Data
US 2015/0335271 A1   Nov. 26, 2015

(30) Foreign Application Priority Data

Jan. 11, 2013   (WO) ................ PCT/CN2013/070349

(51) Int. Cl.
*A61B 5/11*   (2006.01)
*A61B 5/103*   (2006.01)
*A61B 5/00*   (2006.01)

(52) U.S. Cl.
CPC .......... *A61B 5/1121* (2013.01); *A61B 5/0077* (2013.01); *A61B 5/1127* (2013.01); *A61B 2505/05* (2013.01); *A61B 2505/09* (2013.01)

(58) Field of Classification Search
CPC combination set(s) only.
See application file for complete search history.

(56) References Cited

U.S. PATENT DOCUMENTS

| 8,213,678 B2 | 7/2012 | Willmann et al. |
| 9,031,327 B2 | 5/2015 | Yokono |

(Continued)

FOREIGN PATENT DOCUMENTS

| DE | 102010049498 A1 | 5/2012 |
| EP | 2233072 A1 | 9/2010 |

(Continued)

OTHER PUBLICATIONS

"Toledo et al.," "Mechanic criteria for progression in internal and external rotation exercises of the shoulder in the sagittal plane," Rev. bras. Fisioter, San Carlos, v. 11, n. 1, p. 45-52, Jan./Feb. 2007 (Year: 2007).*

(Continued)

*Primary Examiner* — Patricia J Park

(57) ABSTRACT

The present invention provides a system and method for evaluating Range of Motion of a subject. An aspect of the present invention proposes a system for evaluating Range of Motion of a subject, comprising markers attached to at least two joints of a body part of the subject respectively; an image capturing device for capturing images of the markers when the subject is doing an exercise with the body part attached with the at least two markers; and an evaluating device communicated with the image capturing device, wherein the evaluating device includes a determining unit configured to determine whether the exercise done by the subject is valid for the evaluation of Range of Motion of the body part of the subject, and a calculating unit configured to, if the exercise is valid, calculate the parameters related to Range of Motion of the body part of the subject according to the images related to the valid exercise. Thus, the work load of clinicians can be greatly reduced during the process of evaluating Range of Motion, and the accuracy of the evaluation of Range of Motion can be improved as well.

19 Claims, 4 Drawing Sheets

(56) References Cited

U.S. PATENT DOCUMENTS

| | | | | |
|---|---|---|---|---|
| 2002/0170193 | A1* | 11/2002 | Townsend | A61B 5/1116 33/512 |
| 2004/0116837 | A1* | 6/2004 | Yamaguchi | A61B 5/02438 600/595 |
| 2007/0015995 | A1* | 1/2007 | Lang | A61B 5/055 600/407 |
| 2007/0183041 | A1 | 8/2007 | McCloy et al. | |
| 2007/0191746 | A1* | 8/2007 | Barnes | A61F 5/3753 602/4 |
| 2008/0161731 | A1* | 7/2008 | Woods | A61B 5/112 600/595 |
| 2008/0262772 | A1 | 10/2008 | Luinge et al. | |
| 2009/0204030 | A1 | 8/2009 | Brauers et al. | |
| 2009/0259148 | A1 | 10/2009 | Willmann et al. | |
| 2009/0278791 | A1 | 11/2009 | Slycke et al. | |
| 2009/0299232 | A1 | 12/2009 | Lanfermann et al. | |
| 2010/0016766 | A1* | 1/2010 | Zhang | A61F 5/0102 601/5 |
| 2010/0156760 | A1* | 6/2010 | Cheswick | G06F 3/0346 345/31 |
| 2011/0060537 | A1 | 3/2011 | Moodie | |
| 2012/0046901 | A1* | 2/2012 | Green | A61B 5/1126 702/141 |
| 2012/0122063 | A1 | 5/2012 | Chen et al. | |
| 2012/0310075 | A1* | 12/2012 | Russell | A61B 5/1121 600/407 |
| 2013/0137549 | A1* | 5/2013 | Hamada | A63B 24/0087 482/4 |
| 2014/0371634 | A1* | 12/2014 | Jin | A61B 5/1121 600/595 |

FOREIGN PATENT DOCUMENTS

| | | |
|---|---|---|
| JP | 2002000584 | 1/2002 |
| JP | 2007061121 A | 3/2007 |
| KR | 2012017948 A | 2/2012 |
| TW | 201121525 A | 7/2011 |
| WO | 9633472 A1 | 10/1996 |

OTHER PUBLICATIONS

Martinsson, J., et al.; Implementation of motion capture support in smartphones; 2010; Chalmers University of Technology; 89 pages. http://studentarbeten.chalmers.se/publication/129442.

Tao, Y., et al.; Building a Visual Tracking System for Home-Based Rehabilitation; 2003; Proc. of the 9th Chinese Automation and Computing Society Conference in the UK; pp. 443-448.

* cited by examiner

|  | Description | Figure |
|---|---|---|
| Shoulder Abduction | Start position: Parallel to midaxillary line of the trunk<br>Moving position: Anterior aspect of the upper arm parallel to longitudinal axis of the humerus<br>Movement: Shoulder elevation in scapular or frontal plane<br>Range: 30~180° | 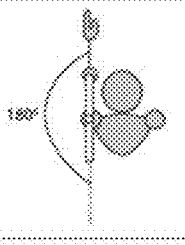 |
| Shoulder Flexion | Start position: Parallel to midaxillary line of the trunk<br>Moving position: Parallel to longitudinal axis of the humerus pointing toward the lateral epicondyle<br>Movement: Shoulder Flexion<br>Range: 30~180° | 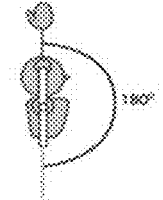 |
| Shoulder Internal/External Rotation | Start position: Parallel to the supporting surface or perpendicular to the floor<br>Moving position: Parallel to the longitudinal axis of the ulna pointing toward the styloid process<br>Movement: Internal and External Rotation<br>Range: internal 0~80°, external 0~60° | 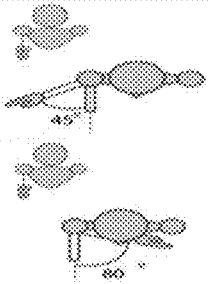 |
| Elbow Flexion | Start Position: Parallel to the longitudinal axis of the humerus pointing towards the tip of the Acromion<br>Moving position: Parallel to longitudinal axis of the radius pointing toward the styloid process of the radius<br>Movement: Elbow flexion<br>Range: 30~150° | 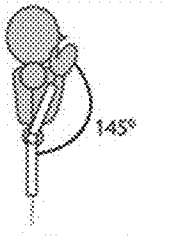 |

FIG. 4

SYSTEM AND METHOD FOR EVALUATING RANGE OF MOTION OF A SUBJECT

FIELD OF THE INVENTION

The invention relates to the field of motion assessment, and particularly to a system and method for evaluating Range of Motion of a subject.

BACKGROUND OF THE INVENTION

Half-sided paralysis (hemiplegy) is one of the most common symptoms of stroke. Post-stroke patients may restore the functional use of limbs by rehabilitation exercises. Clinical scale assessments may be done to get information about health state of the post-stroke patient in order to determine proper rehabilitation exercise plan for the post-stroke patient.

Range of Motion is the most important one of the clinical scale assessments. It is a description of how much movement exists in a body part of the post-stroke patient, and may be evaluated by measuring the number of degrees from the starting position to the end of other full range of the movement. A possible way to measure Range of Motion is with the help of a goniometer. So clinicians are very busy during the process of evaluating Range of Motion: they need keep correcting posture of the patient verbally, at the same time, guiding the patient how to do the evaluation, stopping the patient when the patient cannot reach the target, and using the goniometer to measure the angle.

SUMMARY OF THE INVENTION

It is an object of the present invention to provide an improved system and method for evaluating Range of Motion of a subject.

According to one aspect of the present invention, it provides a system for evaluating Range of Motion of a subject comprising:

markers configured to be attached to at least two joints of a body part of the subject respectively;

an image capturing device for capturing images of the markers when the subject is doing an exercise with the at least two markers attached to the body part, and an evaluating device configured to communicate with the image capturing device, wherein the evaluating device includes a determining unit configured to determine whether the exercise done by the subject is valid for the evaluation of Range of Motion of the body part of the subject, and a calculating unit configured to, if the exercise is valid, calculate the parameters related to Range of Motion of the body part of the subject according to the images related to the valid exercise.

Since the above system is capable of automatically evaluating Range of Motion of a subject, the work load of clinicians can be greatly reduced during the process of evaluating Range of Motion. Moreover, since the validity of the exercise for Range of Motion is determined during this process, the accuracy of the evaluation of Range of Motion can be improved as well.

In accordance with an embodiment of the present invention, the system for evaluating Range of Motion of a subject further comprises a user interface for receiving a signal according to which the evaluating device determines whether the exercise is valid.

In accordance with another embodiment of the present invention, the calculating unit is configured to calculate said parameters according to the coordinates of the markers obtained when the body part is in the maximum movement position and/or the coordinates of the markers obtained when the body part is in the initial position.

In accordance with another embodiment of the present invention, the determining unit comprises:

first subunit for setting standard movement track of one of the joints based on the coordinates of the markers obtained when the body part is in the initial position, and second subunit for determining whether the exercise is valid according to the distance offset between the coordinate of the marker attached to the one of the joints obtained when the body part is in the maximum movement position and a corresponding coordinate in the standard movement track.

In accordance with another embodiment of the present invention, the determining unit comprises subunit for determining whether the exercise is valid according to the time during which the body part keeps in the maximum movement position.

In accordance with another embodiment of the present invention, the determining unit comprises subunit for determining whether the exercise is valid according to the speed of doing the exercise.

According to another aspect of the present invention, it provides a method for evaluating Range of Motion of a subject, wherein markers are attached to at least two joints of a body part of the subject respectively, comprising the steps of:

a) capturing images of the markers by an image capturing device when the subject is doing an exercise with the body part attached with the at least two markers;

b) determining whether the exercise done by the subject is valid for the evaluation of Range of Motion of the body part of the subject; and c) calculating the parameters related to Range of Motion of the body part of the subject according to the images related to the valid exercise if the exercise is valid.

Other objects and advantages of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, wherein:

FIG. 4 is a table showing exercises performed by the subject that are evaluated using the system of FIG. 1.

The same reference signs in the figures indicate similar or corresponding feature and/or functionality.

DETAILED DESCRIPTION

The embodiments of the present invention will be described hereinafter in more detail with reference to the drawings.

Figure 1:
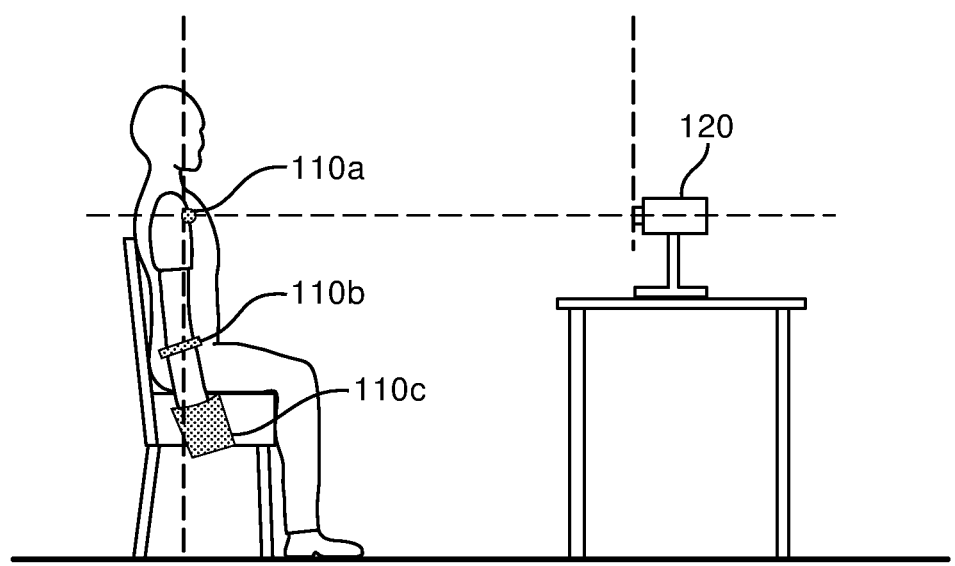
FIG. 1 is a schematic diagram of a system for evaluating Range of Motion of a subject in accordance with an embodiment of the present invention.

FIG. 1 is a schematic diagram of a system for evaluating Range of Motion of a subject in accordance with an embodiment of the present invention, which in the illustrated embodiment includes three markers 110a, 110b, 110c attached to shoulder, elbow and wrist of the subject respectively, and an image capturing device 120 located in front of the subject. In other embodiments, the system may include two, four, or more markers attached to the respective joints of a body part of the subject. The image capturing device 120 is for capturing images of the markers when the subject is doing an exercise with the markers attached to the body part.

Further, the system also includes an evaluating device (not shown) configured to communicate with the image capturing device 120. The evaluating device includes a determining unit configured to determine whether the exercise done by the subject is valid for the evaluation of Range of Motion of the body part of the subject, and a calculating unit configured to, if the exercise is valid, calculate the parameters related to Range of Motion of the body part of the subject according to the images related to the valid exercise. For example, the calculating unit may be configured to calculate these parameters according to the coordinates of the markers obtained when the body part is in the maximum movement position and/or the coordinates of the markers obtained when the body part is in the initial position.

In one illustrative example, the exercises done by the subject may include shoulder abduction exercise, shoulder flexion exercise, shoulder internal/external rotation exercise, and elbow flexion exercise as shown in FIG. 4. Accordingly, the calculation of the parameters related to Range of Motion may be the calculation of the maximum move angles for these exercises.

FIGS. 2a-2e are graphs showing the calculation of the maximum move angles for shoulder abduction exercise, shoulder flexion exercise, shoulder internal/external rotation exercise, and elbow flexion exercise in turn. In FIGS. 2a-2e, the x-axis indicates the direction parallel to the lateral axis of the trunk of the subject, the y-axis indicates the direction parallel to the longitudinal axis of the trunk of the subject, and the z-axis indicates the direction perpendicular to the plane in which the trunk of the subject is located.

Figure 2A:
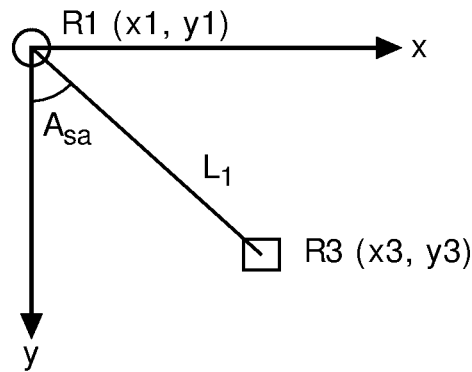
FIGS. 2*a*-2*e* are graphs showing the calculation of the maximum move angles for shoulder abduction exercise, shoulder flexion exercise, shoulder internal/external rotation exercise, and elbow flexion exercise.

As shown in FIG. 2a, the maximum move angle $A_{sa}$ for shoulder abduction exercise may be directly calculated according to the coordinates R1, R3 of the markers 110a, 110c on the x-axis and y-axis obtained when the arm is in the maximum movement position. More specifically, the maximum move angle $A_{sa}$ for shoulder abduction exercise is determined by:

$$A_{sa} = \mathrm{arccot}((y3-y1)/(x3-x1))$$

Figure 2B:
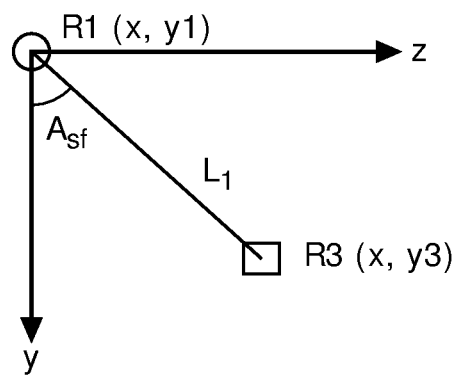
Figure 2C:
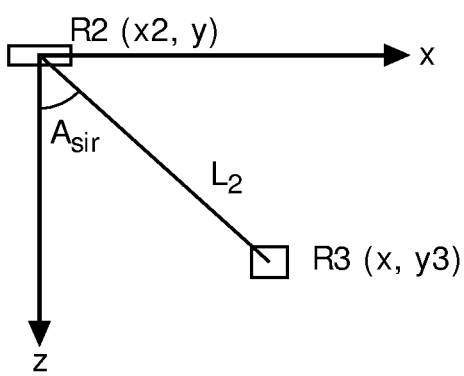
Figure 2D:
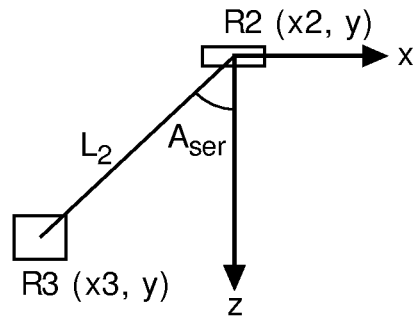
Figure 2E:
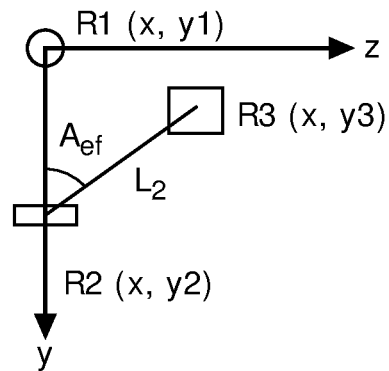

On the other hand, since the images captured by the image capturing device 120 are two-dimensional images, the coordinates of the markers 110a, 110b, 110c on the z-axis cannot be determined. Thus, the maximum move angle $A_{sf}$ for shoulder flexion exercise may be calculated according to the coordinates y1, y3 of the markers 110a, 110c on the y-axis obtained when the arm is in the maximum movement position and the arm length $L_1$, as shown in FIG. 2b. Further, the arm length $L_1$ may be calculated according to the coordinates of the markers 110a, 110c on the x-axis and y-axis obtained when the arm is in the initial position. Thus, the maximum move angle $A_{sf}$ for shoulder flexion exercise is determined by:

$$A_{sf} = \mathrm{arccos}((y3-y1)/(\sqrt{(x3_i-x1_i)^2+(y3_i-y1_i)^2}))$$

Where $x1_i$ and $x3_i$ are the coordinates of the markers 110a, 110c on the x-axis obtained when the arm is in the initial position respectively, and $y1_i$ and $y3_i$ are the coordinates of the markers 110a, 110c on the y-axis obtained when the arm is in the initial position respectively.

Similarly, the maximum move angle $A_{sir}$ for shoulder internal rotation, the maximum move angle $A_{ser}$ for shoulder external rotation exercise, and the maximum move angle $A_{ef}$ for elbow flexion exercise may be calculated according to the coordinates R2, R3 of the markers 110b, 110c on the x-axis and y-axis obtained when the arm is in the maximum movement position and the lower arm length $L_2$. More specifically, the maximum move angles for these exercises are determined by:

$$A_{sir} = \mathrm{arcsin}((x3-x2)/(\sqrt{(x3_i-x2)^2+(y3_i-y2_i)^2}))$$

$$A_{ser} = \mathrm{arcsin}((x2-x3)/(\sqrt{(x3_i-x2_i)^2+(y3_i-y2_i)^2}))$$

$$A_{ef} = \mathrm{arccos}((y3-y2)/\sqrt{(x3_i-x2_i)^2+(y3_i-y2_i)^2})$$

Where $x2_i$ and $y2_i$ are the coordinates of the markers 110b on the x-axis and y-axis obtained when the arm is in the initial position.

According to an embodiment of the present invention, the determining unit may determine whether the exercise done by the subject is valid for the evaluation of Range of Motion of the body part of the subject by means of a first subunit and a second subunit. In particular, the first subunit is used for setting standard movement track of one of the joints based on the coordinates of the markers obtained when the body part is in the initial position, the second subunit is used for determining whether the exercise is valid according to the distance offset between the coordinate of the marker attached to the one of the joints obtained when the body part is in the maximum movement position and a corresponding coordinate in the standard movement track. For example, for the shoulder abduction exercise, the first subunit may set standard movement track (i.e., a semicircular arc) of the wrist based on the coordinates of the markers 110a, 110c obtained when the arm is in the initial position, and the second subunit determines that this exercise is valid in the case that the distance offset between the coordinate of the marker 110c obtained when the arm is in the maximum movement position and a corresponding coordinate in the standard movement track is below a threshold T1 (e.g., 8 cm), wherein the height of the corresponding coordinate with respect to the coordinate of the marker 110c obtained when the arm is in the initial position is equal to the height of the coordinate of the marker 110c obtained when the arm is in the maximum movement position with respect to the coordinate of the marker 110c obtained when the arm is in the initial position.

According to another embodiment of the present invention, the determining unit may include subunit for determining whether the exercise is valid according to the time during which the body part keeps in the maximum movement position. For example, for the shoulder abduction exercise, this subunit may determine that the shoulder abduction exercise is valid in the case that the time during which the arm keeps in the maximum movement position exceeds a threshold T2 (e.g., 3 s).

Additionally, in a further embodiment of the present invention, the determining unit may include subunit for determining whether the exercise is valid according to the speed of doing the exercise. For example, for the shoulder abduction exercise, this subunit may determine that the shoulder abduction exercise is valid in the case that the speed of the wrist is below a threshold T3 (e.g., 32 cm/s) at the moment that the arm is in the maximum movement position. Alternatively, this subunit may determine that the shoulder abduction exercise is valid in the case that the speed of the wrist is always below the threshold T3 during the subject does this exercise.

According to the present invention, the system for evaluating Range of Motion of the subject may include a user interface for receiving a signal according to which the evaluating device determines whether the exercise is valid. For example, if a user finds that the posture of the subject is not abnormal during the subject does an exercise, the user may click "SET" button on a remote controller. Then, the user interface receives a signal emitted from the remote controller, and the evaluating device can determine that the exercise done by the subject is valid according to the received signal.

Figure 3:
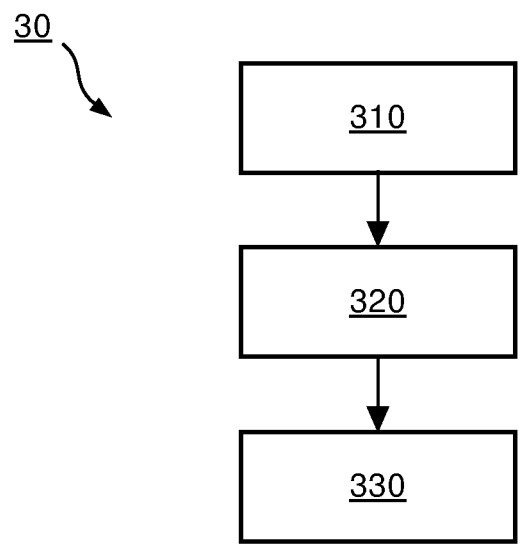
FIG. 3 is a flowchart of a method for evaluating Range of Motion of a subject in accordance with an embodiment of the present invention.

FIG. 3 is a flowchart of the method 30 for evaluating Range of Motion of a subject in accordance with an embodiment of the present invention.

As can be seen from FIG. 3, images of markers are captured by an image capturing device 120 when the subject is doing an exercise with a body part in step 310. The markers are attached to at least two joints of the body part of the subject respectively.

Next, it is determined whether the exercise done by the subject is valid for the evaluation of Range of Motion of the body part of the subject in step 320. Finally, the parameters related to Range of Motion of the body part of the subject are calculated according to images related to the valid exercise if the exercise is valid in step 330.

In accordance with an embodiment of the present invention, the determination of the validity of the exercise for Range of Motion in step 320 may be performed in the following manner. In particular, standard movement track of one of the joints is set based on the coordinates of the markers obtained when the body part is in the initial position. Moreover, it is determined whether the exercise is valid according to the distance offset between the coordinate of the marker attached to the one of the joints obtained when the body part is in the maximum movement position and a corresponding coordinate in the standard movement track.

In accordance with another embodiment of the present invention, the determination of the validity of the exercise for Range of Motion in step 320 may be performed by determining whether the exercise is valid according to the time during which the body part keeps in the maximum movement position or by determining whether the exercise is valid according to the speed of doing the exercise.

Furthermore, in one embodiment, the step 320 may comprise a step of receiving from a user interface a signal indicating whether the exercise is valid. In other embodiments, the step 330 may comprise a step of calculating the parameters related to Range of Motion of the body part of the subject according to the coordinates of the markers obtained when the body part is in the maximum movement position and/or the coordinates of the markers obtained when the body part is in the initial position.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The usage of the words first and second, et cetera, does not indicate any ordering. These words are to be interpreted as names.

The invention claimed is:

1. A system for evaluating range of motion of a subject, the system comprising:
   a plurality of markers configured to be attached to at least two joints of a body part of the subject respectively;
   an image capturing device for capturing images of the markers when the subject is doing an exercise with the markers attached to the body part; and
   a computer including one or more computer processors programmed to:
      receive the images from the image capturing device;
      determine coordinates of the at least two markers in the images when (i) the subject is in a standard movement track of an initial position of the subject before performing the exercise and (ii) the subject is in a maximum movement position while performing the exercise;
      determine a maximum move angle using the determined coordinates of the at least two markers based on the exercise;
      determine whether the exercise is valid for the evaluation of a range of motion of the body part of the subject by:
         (i) determining when a distance offset is below a distance offset threshold, the distance offset being an offset between the coordinate of one of the markers attached to one of the at least two joints in the maximum movement position, and a corresponding coordinate in the standard movement track of one of the at least two joints, the exercise being valid when the distance offset is below the distance offset threshold;
      calculate parameters related to the range of motion of the body part of the subject according to the images related to the valid exercise when the exercise is determined to be valid; and
      output the calculated parameters related to the range of motion to a display of the computer.

2. The system of claim 1, further comprising a user interface for receiving a signal according to which the one or more computer processors are further programmed to determine whether the exercise is valid.

3. The system of claim 1, wherein the one or more computer processors are further programmed to:
   calculate the parameters related to the range of motion according to the coordinates of the markers obtained when the body part is in the maximum movement position and/or the coordinates of the markers obtained when the body part is in the initial position.

4. The system of claim 1, wherein the one or more computer processors are further programmed to determine whether the exercise done by the subject is valid for the evaluation of range of motion of the body part of the subject by:
   (iii) determine a time during which the body part remains in the maximum movement position exceeding a time threshold, the exercise being valid when the time is above the time threshold.

5. The system of claim 1, wherein the exercises include a plurality of:
   a shoulder abduction exercise in which a rRange of mMotion for the subject is 30°-180°;

a shoulder internal rotation exercise in which a range of motion for the subject is 0°-80°;
a shoulder external rotation exercise in which a range of motion for the subject is 0°-60°; and
an elbow flexion exercise in which a range of motion for the subject is 30°-150°.

6. The system of claim 5, wherein the exercise comprises the shoulder abduction exercise, the at least two markers includes a shoulder marker attached to the shoulder of the subject, and a wrist marker attached to a wrist of the patient, and the maximum move angle is determined by:

$$A_{sa} = \text{arccot}((y_3 - y_1)/(x_3 - x_1)),$$

wherein $A_{sa}$ is the maximum movement angle, $x_1$ and $y_1$ are the coordinates of the shoulder marker on corresponding x- and y-axes in the maximum movement position, and $x_3$ and $y_3$ are the coordinates of the wrist marker on the corresponding x- and y-axes in the maximum movement position.

7. The system of claim 5, wherein the exercise comprises the shoulder flexion exercise, the at least two markers includes a shoulder marker attached to the shoulder of the subject, and a wrist marker attached to a wrist of the patient, and the maximum move angle is determined by:

$$A_{sf} = \arccos((y_3 - y_1)/(\sqrt{((x_{3i} - x_{1i})^2 + (y_{3i} - y_{1i})^2)}))$$

wherein $A_{sf}$ is the maximum movement angle, $y_1$ and $y_3$ are the coordinates of the shoulder marker and the wrist marker, respectively, on a corresponding y-axis in the maximum movement position, and $x_{1i}$ and $x_{3i}$ are the coordinates of the shoulder marker and the wrist marker, respectively, on a corresponding x-axis obtained when the subject is in the initial position, and $y_{1i}$ and $y_{3i}$ are the coordinates of the shoulder marker and the wrist marker, respectively, on the y-axis obtained when the subject is in the initial position.

8. The system of claim 5, wherein the exercise comprises the shoulder internal rotation exercise, the at least two markers includes an elbow marker attached to the elbow of the subject, and a wrist marker attached to a wrist of the patient, and the maximum move angle is determined by:

$$A_{sir} = \arcsin((x_3 - x_2)/(\sqrt{((x_{3i} - x_2)^2 + (y_{3i} - y_{2i})^2)}))$$

wherein $A_{sir}$ is the maximum movement angle, $x_2$ and $x_3$ are the coordinates of the elbow marker and the wrist marker, respectively, on a corresponding x-axis in the maximum movement position, $x_{3i}$ is the coordinate of the wrist marker on a corresponding x-axis obtained when the subject is in the initial position, and $y_{2i}$ and $y_{3i}$ are the coordinates of the elbow marker and the wrist marker, respectively, on the y-axis obtained when the subject is in the initial position.

9. The system of claim 5, wherein the exercise comprises the shoulder external rotation exercise, the at least two markers includes an elbow marker attached to the elbow of the subject, and a wrist marker attached to a wrist of the patient, and the maximum move angle is determined by:

$$A_{ser} = \arcsin((x_2 - x_3)/(\sqrt{((x_{3i} - x_{2i})^2 + (y_{3i} - y_{2i})^2)}))$$

wherein $A_{ser}$ is the maximum movement angle, $x_2$ and $x_3$ are the coordinates of the elbow marker and the wrist marker, respectively, on a corresponding x-axis in the maximum movement position, $x_{2i}$ and $x_{3i}$ are the coordinates of the elbow marker and the wrist marker, respectively, on a corresponding x-axis obtained when the subject is in the initial position, and $y_{2i}$ and $y_{3i}$ are the coordinates of the elbow marker and the wrist marker, respectively, on the y-axis obtained when the subject is in the initial position.

10. The system of claim 5, wherein the exercise comprises the elbow flexion exercise, the at least two markers includes an elbow marker attached to the elbow of the subject, and a wrist marker attached to a wrist of the patient, and the maximum move angle is determined by:

$$A_{ef} = \arccos((y_3 - y_2)/\sqrt{((x_{3i} - x_{2i})^2 + (y_{3i} - y_{2i})^2)})$$

wherein $A_{ef}$ is the maximum movement angle, $y_2$ and $y_3$ are the coordinates of the elbow marker and the wrist marker, respectively, on a corresponding y-axis in the maximum movement position, $x_{2i}$ and $x_{3i}$ are the coordinates of the elbow marker and the wrist marker, respectively, on a corresponding x-axis obtained when the subject is in the initial position, and $y_{2i}$ and $y_{3i}$ are the coordinates of the elbow marker and the wrist marker, respectively, on the y-axis obtained when the subject is in the initial position.

11. The system of claim 1, wherein the one or more computer processors are further programmed to, from the determined maximum move angle, determine whether the exercise done by the subject is valid for the evaluation of range of motion of the body part of the subject by:
(ii) determining when a speed of the exercise being performed by the subject is below a speed threshold, the exercise being valid when the speed is below the speed threshold.

12. A method of evaluating range of motion of a subject, wherein markers are attached to at least two joints of a body part of the subject respectively, comprising:
capturing images of the markers by an image capturing device when the subject is doing an exercise with the body part attached with the at least two markers;
determining whether the exercise is valid for the evaluation of range of motion of the body part of the subject by:
determining coordinates of the markers in the images when (i) the subject is in a standard movement track of an initial position of the subject before performing the exercise and (ii) the subject is in a maximum movement position while performing the exercise;
determining a maximum move angle using the determined coordinates of the at least two markers based on the exercise; and
determining whether the exercise is valid for the evaluation of range of motion of the body part of the subject by:
(i) determining when a distance offset is below a distance offset threshold, the distance offset being an offset between the coordinate of one of the markers attached to one of the at least two joints in the maximum movement position, and a corresponding coordinate in the standard movement track of one of the at least two joints, the exercise being valid when the distance offset is below the distance offset threshold; and
calculating parameters related to range of motion of the body part of the subject according to the images related to the exercise when the exercise is determined to be valid.

13. The method of claim 12, wherein the determining comprises receiving from a user interface a signal indicating whether the exercise is valid.

14. The method of claim 12, wherein the calculating comprises calculating the parameters according to the coordinates of the markers obtained when the body part is in the maximum movement position and/or the coordinates of the markers obtained when the body part is in the initial position.

15. The method of claim 12, wherein determining whether the exercise done by the subject is valid for the evaluation of range of motion of the body part of the subject further includes:
(iii) determining a time during which the body part remains in the maximum movement position exceeding a time threshold, the exercise being valid when the time is above the time threshold.

16. The method of claim 12, wherein the exercises include a plurality of:
a shoulder abduction exercise in which a range of motion for the subject is 30°-180°;
a shoulder flexion exercise in which a range of motion for the subject is 30°-180°;
a shoulder internal rotation exercise in which a range of motion for the subject is 0°-80°;
and
an elbow flexion exercise in which a range of motion for the subject is 30°-150°.

17. The method of claim 12, further including, from the determined maximum move angle, determining whether the exercise done by the subject is valid for the evaluation of range of motion of the body part of the subject by:
(ii) determining when a speed of the exercise being performed by the subject is below a speed threshold, the exercise being valid when the speed is below the speed threshold.

18. A system for evaluating range of motion of a subject, the system comprising:
a plurality of markers configured to be attached to at least two joints of a body part of the subject respectively;
an image capturing device for capturing images of the markers when the subject is doing exercises with the at least two markers attached to the body part; and
a computer including one or more computer processors programmed to:
receive the images from the image capturing device;
determine coordinates of the markers in the images when (i) the subject is in a standard movement track of an initial position of the subject before performing the exercise and (ii) the subject is in a maximum movement position while performing the exercise;
determine a maximum move angle using the determined coordinates of the at least two markers based on the exercise;
determine whether the exercise is valid for the evaluation of range of motion of the body part of the subject by:
(i) determining when a distance offset is below a distance offset threshold, the distance offset being an offset between the coordinate of one of the markers attached to one of the at least two joints in the maximum movement position, and a corresponding coordinate in the standard movement track of one of the at least two joints, the exercise being valid when the distance offset is below the distance offset threshold;
calculate parameters related to range of motion of the body part of the subject according to the images related to the valid exercise when the exercise is determined to be valid; and
output the calculated parameters related to range of motion to a display of the computer;
wherein the exercise includes at least:
a shoulder abduction exercise in which a range of motion the subject is 30°-180°;
a shoulder flexion exercise in which a range of motion for the subject is 30°-180°;
a shoulder internal rotation exercise in which a range of motion for the subject is 0°-80°;
a shoulder external rotation exercise in which a range of motion for the subject is 0°-60°; and
an elbow flexion exercise in which a range of motion for the subject is 30°-150°.

19. The system of claim 18, wherein the one or more computer processors are further programmed to, from the determined maximum move angle, determine whether the exercise done by the subject is valid for the evaluation of range of motion of the body part of the subject by:
(ii) determining when a speed of the exercise being performed by the subject is below a speed threshold, the exercise being valid when the speed is below the speed threshold.

* * * * *